United States Patent
Giammona et al.

(10) Patent No.: US 8,529,935 B2
(45) Date of Patent: Sep. 10, 2013

(54) ANTIBACTERIAL HYDROGEL AND USE THEREOF IN ORTHOPEDICS

(75) Inventors: Gaetano Giammona, Palermo (IT); Giovanna Pitarresi, Palermo (IT); Fabio Palumbo, Trabia (IT); Carlo Luca Romano, Milan (IT); Enzo Meani, Milan (IT); Edgardo Cremascoli, Milan (IT)

(73) Assignees: Mero S.R.L., Milan (IT); Novagenit S.R.L., Mezzolombardo (IT)

( * ) Notice: Subject to any disclaimer, the term of this patent is extended or adjusted under 35 U.S.C. 154(b) by 97 days.

(21) Appl. No.: 13/147,153

(22) PCT Filed: Jan. 29, 2010

(86) PCT No.: PCT/EP2010/051117
§ 371 (c)(1),
(2), (4) Date: Jul. 29, 2011

(87) PCT Pub. No.: WO2010/086421
PCT Pub. Date: Aug. 5, 2010

(65) Prior Publication Data
US 2011/0280921 A1 Nov. 17, 2011

(30) Foreign Application Priority Data
Jan. 30, 2009 (EP) .................................... 09151755

(51) Int. Cl.
| | |
|---|---|
| *A61F 2/00* | (2006.01) |
| *A61K 33/00* | (2006.01) |
| *A61K 6/083* | (2006.01) |
| *A61K 31/70* | (2006.01) |
| *A61K 31/715* | (2006.01) |
| *A61K 31/65* | (2006.01) |
| *A61K 31/497* | (2006.01) |
| *A61K 31/44* | (2006.01) |
| *A61K 33/38* | (2006.01) |
| *A61K 33/34* | (2006.01) |
| *A61P 31/00* | (2006.01) |

(52) U.S. Cl.
USPC ........... 424/423; 424/618; 424/638; 424/642; 424/646; 424/78.27; 427/2.26; 514/2.3; 514/25; 514/29; 514/37; 514/61; 514/152; 514/154; 514/210.08; 514/254.11; 514/354

(58) Field of Classification Search
USPC .............. 424/423, 618, 638, 642, 646, 78.27; 427/2.26; 514/2.3, 25, 29, 37, 40, 61, 152, 514/154, 210.08, 254.11, 354, 462, 673
See application file for complete search history.

(56) References Cited

U.S. PATENT DOCUMENTS
2005/0123505 A1* 6/2005 Chen et al. ................. 424/78.27

FOREIGN PATENT DOCUMENTS
| EP | 1 666 518 A1 * | 6/2006 |
| EP | 1 666 518 | 7/2006 |
| WO | WO 2005/032417 | 4/2005 |

OTHER PUBLICATIONS

Christensen et al., "The effects of 'in-use' surgical handwashing on the pre-and postoperative fingertip flora during cardiothoracic and orthopaedic surgery", J. of Hospital Infection 30, pp. 283-293 (1995).
Flückiger et al., "Factors influencing antimicrobial therapy of surface-adhering microorganisms", Recent Res. Devel. Antimicrob. Agents & Chemother. 4, pp. 165-175 (2000).
Palumbo et al., "New graft copolymers of hyaluronic acid and polylactic acid: Synthesis and characterization", Carbohydrate Polymers vol. 66, pp. 379-385 (2006).
Pitarresi et al., "Synthesis of novel graft copolymers of hyaluronan, polyethyleneglycol and polylactic acid", Macromolecules, an Indian Journal vol. 3, No. 2, pp. 53-56 (2007).
Pravata et al., "New Amphiphilic Lactic Acid Oligomer-Hyaluronan Conjugates: Synthesis and Physicochemical Characterization", Biomacromolecules 9, pp. 340-348 (2008).
Gaetano Giammona et al., "New Graft Copolymers of Hyaluronic Acid and Polylactic Acid: Synthesis and Characterization" Carbohydrate Polymers 66, pp. 379-385 (2006).
PCT/EP2010/051117, International Search Report, mailed Apr. 22, 2010, 11 pages.

* cited by examiner

*Primary Examiner* — Blessing Fubara
(74) *Attorney, Agent, or Firm* — DLA Piper LLP (US)

(57) ABSTRACT

The present invention relates to hydrogels endowed with antibacterial properties, to be used for injection in damaged bones or in the production of antibacterial coatings of prostheses for implant in the human or animal body, obtained by loading with antibacterial agents hydrogels formed by derivatives of hyaluronic acid; the invention also relates to a kit of parts for producing the antibacterial hydrogels.

20 Claims, No Drawings

ANTIBACTERIAL HYDROGEL AND USE THEREOF IN ORTHOPEDICS

FIELD OF THE INVENTION

The present invention relates to a hydrogel obtained from derivatives of hyaluronic acid and loaded with antibacterial agents, and its use in the orthopedic field, in particular for the production of antibacterial coatings of prostheses for implant in the human or animal body; the invention also relates to a kit for use of the antibacterial hydrogel.

BACKGROUND OF THE INVENTION

Orthopedics is a branch of surgery dealing with fixation, repairing or reconstruction of damaged bones, also applied in fields such as traumatology, neurosurgery and maxillo-facial surgery.

A technique commonly used in orthopedics is the insertion of implants in the body for the fixation or reconstruction of bones and their parts. Implants are generally made of biocompatible metals (in particular titanium, cobalt-chrome, etc.), polymers, ceramics, hydroxyapatite, or their combinations (e.g., metals coated with a layer of hydroxyapatite). The technique is generally used in osteosynthesis, joint replacements, orthopedic and traumatological bone reconstruction, spine surgery and maxillo-facial and odonthoiatric applications. Implants may be used to replace, at least partially, damaged bones, joints or teeth; or, they may be aid means used to fix bone parts or help these to keep the correct spatial relationship; in this second case the implants may be bone fixation plates (e.g., craniofacial, maxillo-facial, orthopedic, skeletal and the like), nails, screws, scaffolds and the like. The term "prosthesis" would be more appropriate for devices of the first kind, but as used in the present invention, it will be intended to mean both an actual prosthesis and any other aid means to be inserted in the human or animal body for the applications cited above.

Another technique adopted in orthopedics is the injection of biocompatible materials in damaged parts of bones, such as fractures or holes; the latter may result by the removal from bones of temporary implants, such as screws. The biocompatible material in this case has the function of temporarily replace the bone tissues, in order to maintain mechanical resistance, for the period necessary for such tissues to grow and fill the damaged area or space.

Bacterial infections due to implanted or injected biomaterials still represent a serious complication in orthopedic surgery. Many studies have documented the transfer of organisms from personnel in the operating theater to the patient during surgical interventions; see, e.g., Bather C. J. et al, "The effects of 'in-use' surgical handwashing on the pre- and postoperative fingertip flora during cardiothoracic and orthopaedic surgery", Journal of Hospital Infection, (1995) 30, 283-293.

Acute or chronic osteomyelitic infections may also develop in many cases of osteosynthesis after bone fractures. In situations in which an inert foreign body is implanted into an already injured and weakened tissue, a competition develops for the colonization of the implant surfaces between bacteria (such as *Staphylococcus Aureus*, which has often been found in cases of contaminated bone fractures) and the cells of the immune system. However, bacteria have the advantages over immune system cells of faster reproductive processes and an extreme flexibility in adapting to the environment. Moreover, studies indicate that the procedures for implanting a prosthesis, and the presence of the prosthesis itself in the site of bone fracture, damage the response of the local immune system with the result that the number of bacteria required to cause an infection can fall by a factor of even 10,000 (Flückiger U. et al, "Factors influencing antimicrobial therapy of surface adhering microorganisms", Recent Res. Devel. Antimicrob. Agents Chemother., (2000) 4, 165-175).

A standard implantation technique for prostheses and osteosynthesis consists of extensive removal of the necrotic and damaged tissue, cleaning of the cavity, implanting of a prosthesis and systemic parenteral prophylaxis with antibiotics. Similar procedures are adopted in case of injection of fluid biomaterials in fractures or bone cavities. The systemic release of antibiotics involves certain drawbacks such as systemic toxicity, reduced absorption into the ischemic or necrotic tissues and prolonged hospitalization to monitor drug levels and its effects. In cases in which bacterial colonization of the treated part is not efficiently avoided by systemic prophylaxis, a new surgical intervention (especially in case the replacement of the prosthesis is necessary), and an extension of the hospitalization period may be required, resulting in further discomfort for the patient.

In order to avoid these drawbacks, local antibiotic therapy has become an accepted and common alternative or adjunct to systemic antibiotic therapies, for prophylaxis and prevention of bacterial infections derived from orthopedic surgical interventions. Local antibiotic therapy offers various advantages over systemic therapy, including: a high active principle concentration at the infection site while eliminating systemic toxicity; a more thorough eradication of the infection; and the use of smaller drug doses which do not cause toxic effects.

For the aforesaid reasons, several researchers have proposed antibacterial materials with non-fouling properties, in particular for use as coatings of the orthopedic prostheses; such materials should preferably be capable to release an active principle immediately after the intervention and at least during the following 6 hours, preferably up to 48-72 hours, so as to cover the critical period of possible bacteria attack and proliferation in the intervention site.

Various carriers for local drug release have been developed and used, such as polymethylmethacrylate (PMMA) beds onto which the drug is loaded. These materials are however not reabsorbed and require subsequent intervention for their removal. Moreover the low porosity of the PMMA bed inhibits drug release by 25-50%, thus reducing the drug quantity released and increasing the risk of selection of bacterial mutants resistant to the active principle.

Biodegradable materials offer the advantages of bioreabsorption, which avoids subsequent intervention to remove them, reduces reactions induced by foreign bodies, and increases total release of the drug locally; besides, the kinetics of drug release from the matrix can be modulated by controlling the matrix degradation processes.

A known biodegradable and bioreabsorbable polymer is hyaluronic acid. Hyaluronic acid (also indicated as HA in the rest of the description) is a generic name for polysaccharides deriving from the polymerization of a repeating unit comprising D-glucuronic acid and N-acetyl-D-glucosamine. HA, in the forms naturally occurring in many animal tissues, may have a molecular weight (MW) ranging from about 5,000 to about 20 millions Dalton (Da), and the properties of a specific sample of the compound may vary depending on its actual MW. HA is a fundamental component of the extracellular matrix (ECM) and is essential for good operation of numerous body tissues such as connective or epithelial tissues, and in the inner ear fluids, in the vitreous humour of the eyes and also in the liquid essential for the joints (synovia). It is a highly biocompatible and biodegradable polymer with well known anti-adhesive and lubricity properties, the latter exploited in International patent application WO 2004/014303. However, HA as such is not suitable for injection or for the coating of prostheses, due to its rapid degradation by hyaluronidases, enzymes naturally occurring in the human and animal body; as a consequence of such rapid degradation, drug release over the required period can not be guaranteed. Furthermore, due to its high hydrophilicity, a coating produced with HA would not have sufficient mechanical stability when a prosthesis is implanted in the body, that is, an essentially water-based environment.

HA derivatives have been studied in view of various possible medical applications.

International patent application WO 2006/069578 discloses copolymers of HA with polymers of alpha hydroxyl acids or other polymers, for different uses in the cosmetic or medical field; this document does not cite the use of these HA-based copolymers for injection or the treatment of prostheses.

Patent EP 1773399 B1 discloses compositions obtained by the cross-linking of HA with a polyhydrazide; these compositions form hydrogels when contacted with water.

Patent application US 2004/0013626 A1 discloses nanoparticles to be used as drug vectors, formed of a polymer obtained by grafting at least one molecule of a polysaccharide to a biodegradable polymer different from the polysaccharide, preferably a polyester.

The paper "New amphiphilic lactic acid oligomer-hyaluronan conjugates: synthesis and physicochemical characterization", Pravata L. et al, Biomacromolecules (2008) 9, 340-348, describes a HA derivative produced by grafting lactic acid oligomers (OLA), of average molecular weight around 500 Da, to hydroxyl radicals of the acid. These HA-OLA derivatives show lower hydrophilicity than HA and modified rheological properties compared to the same, making them more stable in an aqueous ambient, while maintaining good biodegradability and bioreabsorption characteristics.

The paper "New graft copolymers of hyaluronic acid and polylactic acid: synthesis and characterization", Palumbo F. S. et al, Carbohydrate Polymers (2006) 66, 379-385, describes HA derivatives obtained by grafting poly-lactic acid (also abbreviated PLA in the rest of the description) to a HA of average MW of 266,000 Da with two different substitution degrees, in the first case a ratio PLA chains to HA repeating units of 1.5%, in the second case a substitution degree of 7.8%; the first compound is still rather hydrophilic, while the second is more hydrophobic and gives rise to gel-like dispersions in water. This paper indicates some possible applications of the disclosed graft copolymers in the biomedical field, such as the use of their aqueous solutions to reduce adhesion after abdominal surgery, in ophthalmic procedures and for the lubrication of joints, but no hint is given to possible uses in orthopedic implants.

The paper "Synthesis of novel graft copolymers of hyaluronan, polyethyleneglycol and polylactic acid", Pitarresi G. et al, Macromolecules an Indian Journal, Vol. 3, Issue 2, August 2007, 53-56 describes HA derivatives obtained by grafting onto the HA chain both PLA and polyethylene glycol (abbreviated PEG), showing that these latter are less hydrophobic than compounds obtained by HA and PLA alone.

International patent application WO 2005/032417 discloses a coating produced using a physical mixture of HA with one or more biocompatible polymers, among which PLA, and loaded with an antimicrobial agent; this document also discloses the use of said mixture to produce a dry film charged with the antimicrobial agent onto the surface of a prosthesis, for subsequent implant. Prostheses coatings produced according to this document however suffer of at least two drawbacks: first, the antimicrobial agent, e.g. an antibiotic, has a limited lifetime, so it may not be completely efficient at the time of implant; second, this method does not allow to tailor the prosthesis coating to the specific requirements of the different cases, for instance, known intolerances of a patient to a given antibiotic, or the need to adopt a particular antibiotic, or a specific level of dosage of the same, in a specific situation.

Finally, patent application EP 1666518 A1 discloses drug carriers derived from a HA modification product, in which polyester chains (selected from polylactic acid, polyglycolic acid, and lactic acid-glycolic acid copolymers) are grafted onto the base HA chain. As stated in this document, and shown in all the formulas shown therein, the grafting of the polyester to the HA chain occurs by bonding, either directly or through di-amino or di-hidrazide spacers, to the carboxilic groups present on the glucuronic acid moieties of HA. This way, at least part the carboxilic groups of HA are transformed into amide groups; as the free carboxilic groups are responsible of the hydrophilicity of HA, the modification proposed in this document leads to a reduction of said hydrophilicity; in fact, the modified HA chains of EP 1666518 A1 exhibit a tendency to coil on themselves, making these products suitable for the production of micro- or nanospheres used as injectable drug carriers according to an aspect of the invention disclosed in the cited document. Besides, the compositions disclosed in this document are aimed and tailored to the sustained release of the drug, during a period longer than several days (see paragraph [0007] of the document), but this feature is not desirable in the specific field of orthopedics.

There is thus a need in the field for improved antibacterial materials for use in orthopedic surgery, not suffering the drawbacks of the prior art.

SUMMARY OF THE INVENTION

It is thus an object of the invention to provide a hydrogel comprising a hyaluronic acid derivative and an antibacterial component having improved properties of chemical-mechanical stability and release of the antibacterial component, a method for the use of said hydrogel in orthopedic surgery, and a kit for use in said method.

DETAILED DESCRIPTION OF THE INVENTION

According to its first aspect, the invention provides an antibacterial hydrogel comprising water, a hyaluronic acid derivative and an antibacterial agent, wherein:
  the hyaluronic acid derivative comprises hyaluronic acid, or a salt thereof, of molecular weight comprised between 50,000 and 3,500,000 Da onto the N-acetyl-D-glucosamine moieties of which are grafted chains of a biodegradable and biocompatible polyester of molecular weight comprised between 3,000 and 900,000 Da, in an amount such that the derivative comprises between 1 and 15 of said polyester chains per 100 repeating unit D-glucuronic acid/N-acetyl-D-glucosamine of hyaluronic acid;
  the hyaluronic acid derivative concentration is between 1 and 30% w/v; and
  the antibacterial agent is chosen among antibiotics, antifungals metal ions and their combinations, and has a concentration between 0.001% and 80% w/v.

As the final hydrogel is obtained by adding an antibacterial agent to another hydrogel, in order to distinguish the two, in the following description the hydrogel not containing the antibacterial agent will be simply referred to as "hydrogel", while the hydrogel to which the antibacterial agent has been added will be referred to with the term "antibacterial hydrogel". Besides, all percentages in the following description are expressed as weight/volume (w/v, indicating the mass of solute in grams per 100 ml of the resulting solution or gel) unless specified otherwise.

The inventors have found that, starting from a particular class of HA derivatives, it is possible to produce a stable hydrogel that can be charged with desired amounts of an antibacterial agent, useful for injection in bone fractures or cavities and for the production of coatings of prostheses that are endowed with a mix of chemical, mechanical and antibacterial agent-release properties well suited for the intended use. Though the rest of the description will be made with reference to hyaluronic acid, it is understood that by this term are meant as well salts of the acid normally present in a human or animal body, such as salts of $Na^+$, $K^+$, $Mg^{2+}$ or $Ca^{2+}$. In particular, the inventors have found that by grafting the biocompatible polyester onto the N-acetyl-D-glucosamine moieties of HA, through reaction with the free hydroxy group present in these moieties, the HA derivative maintains high hydrophilicity, combined with properties of viscosity and retention of this viscosity with time, as well as fast release of the antibacterial agent, that make these derivatives extremely well suited for applications in the orthopedics field. This is contrary to the teaching of the cited document EP 1666518 A1, in which the grafting of polyester side-chains take place onto the carboxilic acid groups instead, leading to a reduced hydrophilicity.

The main component of the hydrogel is a hyaluronic acid derivative, obtained by grafting chains of biodegradable and biocompatible polyesters onto a fraction of the acid having molecular weight in a particular range.

The useful fraction of HA, to be used as starting material in the preparation of the derivative, has a molecular weight (MW) comprised between about 50 kDa and 3.5 MDa, preferably between 100 kDa and 1.5 MDa and more preferably of about 200-300 kDa. HA of MW in these ranges may be obtained by degradation of higher fractions of HA in strongly acid environments, as described in the paper "Disulfide crosslinked hyaluronan hydrogel", Shu X. Z. et al, Biomacromolecules (200) 3, 1304-1311. The starting material may be obtained from natural sources (e.g., rooster combs); in alternative, it may be produced by microorganisms (as described e.g. in U.S. Pat. No. 4,801,539 and EP 694616) or from recombinant routes (as described e.g. in patent applications WO 03/054163 and WO 2006/069578). Synthetic pathways (from microorganisms or recombinant route) may also be adapted to produce HA already in the desired MW range, that thus does not need a degradation step.

The other reactant in the production of the derivative is a biodegradable and biocompatible polyester or a mixture of polyesters or copolymers thereof. The most interesting polyesters for the aims of the invention are poly-lactic acid, poly-glycolic acid, poly-caprolactone (these latter also referred to in the rest of the description as PGA and PCL, respectively), their mixtures and copolymers. It has been found that hydrogels of desired properties can be prepared with HA derivatives produced with polyesters having a MW in the range between 3-150 kDa in the case of PLA, in the range 1-900 kDa in the case of PGA, and in the range 3-900 kDa in the case of PCL or of copolymers PLA-PGA (also referred to as PLGA hereinafter) or copolymers comprising PCL. These compounds are commercially available, for instance from Boehringer Ingelheim or from resellers of chemicals, such as Fluka or Sigma-Aldrich.

In order to enhance the reactivity of the polyester, it is preferable to activate its carboxylic end by reaction with a good leaving group, e.g. an imide, preferably N-hydroxysuccinimide (NHS). The formation of these polyester-NHS compounds is carried out through a first reaction of the free carboxyl group of the polyester with dicyclohexylcarbodiimide (DCC) and then functionalizing it with NHS; the reaction is carried out, e.g., at room temperature for 24 hours.

Owing to the fact that HA is a strongly hydrophilic compound, while the above polyesters (even when activated with NHS) are hydrophobic, it is necessary to render one of the reactants compatible with the solvents suitable for the other reactant. According to the present invention, this result is obtained by transforming HA into an ammonium salt, such as the cetyltrimethylammonium (CTA) or preferably the tetrabutylammonium (TBA) salt. The formation of the ammonium salt may be simply carried out by neutralizing HA with the hydroxide of the ammonium cation. The reaction proceeds with 100% yield, and the resulting product in soluble in dimethyl sulfoxide (DMSO), in which the polyesters and their —NHS derivatives are soluble as well. In case HA is available in the form of one of its inorganic salts (e.g., the sodium salt, the most common commercial form of HA), it is possible to first pass an aqueous solution of the same through an acid ion-exchange column, or treat it with an acid, in order to recover HA in acid form.

The ammonium-substituted HA and the polyester-NHS compound are then reacted in DMSO in the presence of diethylamine (DEA) as a catalyst; the reaction takes place e.g. in 24 hours at 40° C. The reaction consists in the condensation of the carboxylic function of the polyester (activated with NHS) with the hydroxyl group of the N-acetyl-D-glucosamine units of HA. The ratio of N-acetyl-D-glucosamine units to which is grafted a polyester chain to the total number of such units present in the HA is defined in the present invention "derivatization degree". The inventors have found that hydrogels of desired properties can be produced with HA derivatives in which said derivatization degree is comprised between 1 and 15%.

The properties (in particular the hydrophilicity and anti-fouling characteristics) of the HA derivative may be further modulated through a second derivatization, in which a part of the carboxyl groups of the D-glucuronic acid of HA are functionalized with polyethylene glycol (PEG) chains. PEG is known to be a biocompatible polymer (it is approved by the FDA) and is widely used in the pharmaceutical field both for preparing conventional dosage forms and for innovative release systems. Best final results are obtained when the PEG employed has a MW between 400 Da and 20 kDa, preferably of about 5 kDa, and the derivatization degree of HA with PEG (namely, the ratio of D-glucuronic acid units derivatized with PEG to the total number of such units in the HA) is comprised between 5 and 20%.

PEG is preferably pre-activated, to enhance its reactivity, through exchange of the free —OH group at one end thereof with —$NH_2$ (PEG-$NH_2$); this latter compound is also available commercially. PEG-$NH_2$ is added in DMSO to the reaction product of ammonium-substituted HA and polyester-NHS, after the latter has been isolated by precipitation of the reaction mixture with a non-polar solvent (e.g., diethyl ether), filtration and repeated washing with acetone to eliminate any non reacted polyester-NHS.

The HA derivatives thus obtained (with or without PEG) are then purified by means known to the skilled in the art, e.g., dialysis and freeze-drying, and possibly subjected to ion exchange to exchange the ammonium ions with $Na^+$ or $K^+$ ions, more compatible with the intended use.

The HA derivative is then added to water (normally bidistilled water, a NaOH solution of concentration between 0.075 and 0.75 M, or a physiological solution), in such an amount that its concentration in the resulting hydrogel, before addition of the antibacterial agent, is comprised between 1 and 35% w/v, preferably between 2 and 10% w/v. Operating as described so far, all concentrations of HA derivative between 1 and 35% w/v give rise to uniform transparent viscous gels. These hydrogels are stable for long periods, and can be stored for at least six months even at ambient temperature without altering their properties, in particular their viscosity.

The final step in the preparation of the antibacterial hydrogel of the invention is the addition of one or more antibacterial agent(s) chosen among known antibiotics, antifungals and metal ions, in such an amount that their concentration in the antibacterial hydrogel is comprised between 0.001% and 80% w/v.

Examples of suitable antibiotics are daptomicin, tigecycline, telavancin, chloramphenicol, fusidic acid, bacitracin, rifampin, ethambutol, streptomycin, isoniazid, and all those comprised in the following antibacterial families: glicopeptides (including but not limited to teicoplanin, vancomycin, etc.), aminoglicosydes (including but not limited to, gentamycin, tobramycin, amikacin, netimicin, etc.), cephalosporins (including but not limited to cefazolin, cefoxitin, cefotaxime, cefuroxime, moxalactam, etc.), macrolids (including but not limited to erythromycin), oxazolidinones (including but not limited to linezolid), quinolones, polymixins, sulfonamides, tetracyclines and penicillins.

Useful antifungals are those comprised in the followings families: polyene antifungals, imidazole and triazole antifungals, allylamines, echinocandines, griseofulvine.

Examples of metals whose ions have antibacterial activity are silver and nanosilver formulations, zinc, copper, cobalt, nickel.

In case of the metals, these may be added to the hydrogel directly during the previous step of addition of water to the HA derivative, in the form of their soluble salts in water, whose anions are biocompatible, such as the nitrates.

On the other hand, antibiotics are preferably added to the hydrogel soon before its use: this gives rise to the several advantages of the present invention compared to known systems, in that it is possible to add the antibiotic only at the moment when it is needed, thus avoiding the problems of shelf-life of the treated prostheses of WO 2005/032417; besides, it is possible to choose the optimal antibiotic in the specific case, taking into account patient's specificity; finally, it is possible to decide the dosing of the antibacterial agent on a case-by-case basis (this advantage being present also in the case of metal ions).

The antibacterial hydrogels of the invention have a rate of reabsorption in the body such that the release of the antibacterial agent always lasts at least 6 hours after the orthopedic intervention, that are the most critical from the point of view of bacterial attack; often, the release of antibacterial agent is prolonged for 48-72 hours, so as to cover the first days after said intervention.

In its second aspect, the invention provides a method for the use of the antibacterial hydrogel previously described in orthopedic surgery.

According to the method, the antibacterial hydrogel is produced just before its use, by mixing the hydrogel of the HA derivative with the chosen antibacterial agent in the desired ratio; and, in a short term after its preparation, injected in the area of bone fracture or cavity or applied to the surface of a prosthesis to be implanted. The injection into bone damaged parts may be realized by a needle and a syringe, under ecographic guide. The application of the antibacterial hydrogel onto the prosthesis may be realized by various methods, such as immersion of the prosthesis into the hydrogel, spraying, spreading, brushing and the like.

In its last aspect, the invention is about a kit for use in the above disclosed method. The kit is composed of two compositions, the first being the hydrogel formed by the HA derivative and water, the second being the antibacterial agent or a solution or suspension in a suitable means of the antibacterial agent.

The antibacterial hydrogel has a concentration in the HA derivative comprised between 1 and 30% w/v, preferably between 2 and 10% w/v, and a concentration in the antibacterial agent comprised between 0.001% and 80% w/v, preferably between 1 and 10% w/v. To obtain these final concentrations, the two compositions making up the kit may have concentrations in wide ranges and be mixed in different ratios, as it will be apparent to the skilled technician. In more common cases, the volume of HA derivative composition used is greater than the volume of solution of antibacterial agent; for this reason, the concentration of the starting HA derivative composition will be close to the concentration of the same derivative in the antibacterial hydrogel, and is comprised between 1 and 35% w/v, preferably 2-10% w/v. To the contrary, the concentration of the starting antibacterial agent composition may greatly differ from the concentration of said agent in the antibacterial hydrogel (it may even be 100% in case said second composition is the antibacterial agent in pure form).

According to common embodiments of the invention, in preparing the antibacterial hydrogel, the HA derivative and the antibacterial agent solution are mixed in a volume ratio comprised between 20:1 and 1:1, preferably between 10:1 and 1.5:1. To avoid that parts of the antibacterial hydrogel are not sufficiently loaded with the drug, the mixture formed by the two compositions is preferably homogenized by stirring or mixing, that can simply be done manually or with automatic means.

The kit of the invention makes it possible for the surgeon to decide the actual loading of antibacterial agent in the antibacterial hydrogel, both as to the nature of said agent and to its concentration, just before or even during the surgical intervention, allowing the best tailoring of the antibacterial injection material or coating onto the prosthesis, in view of the specific needs of the patients (e.g., known intolerances to specific antibacterial agents) or of the specific intervention. For instance, good results have been obtained combining compositions of the HA derivative at concentration of about 5% w/v with antibacterial compositions containing vancomycin at concentration between 10 and 20% w/v in a volume ratio of about 9:1; or, combining compositions of the HA derivative at a concentration of 7.5% w/v with antibacterial compositions containing tobramycin at a concentration of about 5% w/v in a volume ratio of about 4:1.

The invention will be further illustrated by means of the following examples, intended to assist in understanding the invention and not to be construed as specifically limiting the invention described and claimed herein.

In the examples, the following materials and equipments have been used:

Materials:

The sodium salt of hyaluronic acid (MW 1500 kDa), vancomycin, tobramycin and the titanium prostheses coated with hydroxyapatite have been provided by NOVAGENIT s.r.l. (Milan, Italy). D,L-polylactic acid (PLA) (MW 8 kDa) is sold by Bidachem-Boeringher Ingelheim (Milan, Italy) with the name RESOMER R 202. N,N'-Dicyclohexylcarbodiimide (DCC), N-hydroxysuccinimide (NHS), tetrabutylammonium hydroxide (TBA-OH), hydrochloric acid, the Dulbecco's phosphate buffered saline (DPBS pH 7.4) and the reagent in o-phthaldialdehyde (OPA) solution were purchased from Sigma Aldrich (Milan, Italy). The Dowex 50W×8-200 cation exchange resin, diethylamine (DEA), anhydrous dimethyl sulfoxide (DMSO) and O-2-aminoethyl-O'-methylpolyethylene glycol 5000 (PEG-NH$_2$) were obtained from Fluka (Milan, Italy).

Equipments:

The $^1$H-NMR spectra were obtained with a Brucker AC-300 instrument. High performance chromatographic analysis (HPLC) was carried out using an Agilent 1100 Series liquid chromatograph equipped with an Agilent 7725i injector (provided with a loop of 20 μL) and with an Agilent 1100 series UV detector of variable wavelength interfaced with a computerized station. The chromatography column was a reversed phase Agilent Zorbax Eclipse XDB C8 with inner diameter 46 mm×150 mm produced by Agilent. To evaluate the release of vancomycin, the mobile phase used was 5 mM potassium dihydrogen phosphate pH 2.8/acetonitrile (96:4), flow 1 ml/min; the eluate originating from the column was determined at a wavelength of 280 nm. To evaluate the tobramycin release, the mobile phase used was 0.02 M phosphate pH 6.5/acetonitrile 52:48, flow 1 ml/min; as tobramycin does not absorb ultraviolet light, a reaction was carried out between the sample to be analyzed and the reagent OPA; the eluate originating from the column was determined at a wavelength of 254 nm. The FT-IR spectra were recorded as KBr discs in the range 4000-400 cm$^{-1}$ using a Perkin Elmer spectrophotometer 1720 and Fourier transformed, with a 1 cm$^{-1}$ resolution; each spectrum was recorded after 100 scans. SEC analysis was carried out using a SEC multidetector system equipped with a Water 600 pump, a Water 410 refractive index meter, and a linear column provided by Water (particle size 5 μm). The calibration curve was determined using hyaluronic acid standards purchased from Hyalose (USA). The elution conditions were the following: phosphate buffer 200 mM (pH 6.5)/MeOH 90:10 (v/v), flow rate 0.6 ml/min, at a temperature of 35° C.

EXAMPLE 1

This example is about the formation of the tetrabutylammonium salt of HA (HA-TBA).

1 g of HA of molecular weight 1500 kDa are dissolved in 100 ml of a HCl solution having pH 0.5, and left to react at 37° C. for 24 hours. The resulting product has an average MW of 230 kDa, as determined by SEC analysis. To this product, tetrabutylammonium hydroxide (TBA-OH) is added until pH 7 is reached; the reaction mixture is then subjected to exhaustive dialysis.

The resulting HA-TBA salt is recovered by freeze drying and characterized by $^1$H-NMR (D$_2$O) analysis which confirms that exchange with TBA has taken place with a yield of 100%. The $^1$H-NMR (D$_2$O) spectrum of the HA-TBA shows signals at: δ 0.97 (m, 12H, N$^+$—(CH$_2$—CH$_2$—CH$_2$—CH$_3$)$_4$); δ 1.40 (m, 8H, N$^+$—(CH$_2$—CH$_2$—CH$_2$—CH$_3$)$_4$); δ 1.64 (m, 8H, N$^+$—(CH$_2$—CH$_2$—CH$_2$—CH$_3$)$_4$); δ 2.04 (s, 3H, —NH—CO—CH$_3$); δ 3.82 (m, 8H, N$^+$(CH$_2$—CH$_2$—CH$_2$—CH$_3$)$_4$).

EXAMPLE 2

This example is about the activation of a polyester (PLA) with NHS.

The synthesis is carried out following the synthesis route of polylactic-co-glycolic acid (PLGA) derivative described in the paper "Folate receptor targeted biodegradable polymeric doxorubicin micelles", Yoo H. S. et al, Journal of Controlled Release, (2004) 96: 273-283.

2.4 g of PLA of average MW 8 kDa are dissolved in 30 ml of dichloromethane. To this solution are first added 0.25 g of the condensing agent dicyclohexylcarbodiimide (DCC), and then 0.14 g of NHS, allowing the reaction to take place at ambient temperature for 24 hours. After this period, the reaction mixture is concentrated by partial evaporation of dichloromethane and the product is precipitated in ethanol and repeatedly washed in the same solvent. The solid obtained is then filtered off and dried under vacuum. A white crystalline solid is obtained, with a yield exceeding 80% by weight on the starting PLA quantity. The $^1$H-NMR spectrum confirms that activation of the PLA carboxyl group with N-hydroxysuccinimide has taken place. The yield of derivatization, expressed as the ratio of bound moles of NHS to moles of a single PLA chain, is 90%.

The $^1$H-NMR spectrum of the product PLA-NHS (CDCl$_3$) shows signals at: δ 1.5 and δ 1.6 (d, 3H, —O—CO—CH(CH$_3$)—OH; δ, 3H, O—CO—CH(CH$_3$)—O—), δ 2.80 (m, 4H, —OC—CH$_2$—CH$_2$—CO—); δ 4.3 and δ 5.2 (m, 1H, —O—CO—CH(CH$_3$)—OH; m, 1H, —O—CO—CH(CH$_3$)—O—).

EXAMPLE 3

This example is about the synthesis of a HA-PLA derivatives.

HA-TBA prepared as described in Example 1 and PLA-NHS prepared as described in Example 2 are reacted in three different ratios, to obtain products of different PLA-derivatization degree. Three HA-TBA solutions of same concentration are obtained by dissolving for each solution 600 mg of HA-TBA in 48 ml of anhydrous DMSO in the presence of 576 μl of the catalyst diethylamine (DEA). Apart, three solutions of different concentration of PLA-NHS are prepared by dissolving, respectively, 1.5, 3.6 and 7.2 g of PLA-NHS in 6 ml of anhydrous DMSO. The three PLA-NHS solutions are added dropwise over a one hour period to the HA-TBA solutions; the nominal ratio of moles of PLA-NHS to moles of N-acetyl-D-glucosamine units of HA in the three reacting mixtures is 0.2, 0.5 and 1.0, respectively. The three different derivatives are named in the following HA-PLA$_{(A)}$, HA-PLA$_{(B)}$ and HA-PLA$_{(C)}$.

After 24 hours under an anhydrous argon atmosphere 40° C., each reaction mixture is passed through a Dowex sodium exchange resin to exchange the TBA with Na$^+$. The eluate is then placed under dialysis against distilled water to eliminate DMSO, then frozen and dried by freeze-drying. The solid is washed repeatedly in acetone and dried again.

The FT-IR spectrum of the obtained HA-PLA derivatives shows a band at 3540 cm$^{-1}$ ($v_{as}$ OH+$v_{as}$ NH of HA), bands at 1757 cm$^{-1}$ ($v_{as}$ COO of PLA), 1623 cm$^{-1}$ (amide I of HA), 1456 cm$^{-1}$ ($v_{as}$, CH$_3$ of PLA), 1382 cm$^{-1}$ ($v_s$ CH$_3$ of PLA), 1189 cm$^{-1}$ ($v_s$ C—O—C of the ester groups of PLA), 1089 cm$^{-1}$ and 1048 cm$^{-1}$ ($v$ C—O alcoholic and etheric of HA).

The $^1$H-NMR spectrum of the obtained HA$_{LMW}$-PLA derivatives (DMSO-d$_6$/D$_2$O 90:10) shows: δ 1.25 and δ 1.45 (2d, —O—CO—CH(CH$_3$)—O— of PLA); δ 1.85 (s, 3H, —NH—CO—CH$_3$ of HA) δ 5.1 ppm (m, —O—CO—CH(CH$_3$)— of PLA).

The derivatization degree (DD, %) in PLA of the HA-PLA derivatives is calculated by evaluating the number of PLA chains from the integrals of the two peaks relative to the protons at δ 1.25 and δ 1.45 (attributable to the methyl groups of the PLA chain) and the number of N-acetyl-D-glucosamine present in the HA from the integral relative to the protons at δ 1.85 attributable to the —NHCOCH$_3$ group, and then applying the formula:

DD=(No. moles PLA/No. moles glucosamine units)×100,

The results of derivatization degree for the three different reaction mixtures are as given in Table 1:

TABLE 1

| Sample | DD (%) in PLA |
|---|---|
| HA-PLA$_{(A)}$ | 2.7 |
| HA-PLA$_{(B)}$ | 3.5 |
| HA-PLA$_{(C)}$ | 7 |

EXAMPLE 4

This example is about the synthesis of a PEG-HA-PLA derivatives.

The preparation of HA-PLA derivatives described in Example 3 is repeated, with the differences that in this case are used three solutions obtained by dissolving in 6 ml of anhydrous DMSO, respectively, 5.2, 7.2 and 14.0 g of PLA-NHS (corresponding to nominal ratios of moles of PLA-NHS to moles of N-acetyl-D-glucosamine units of HA of 0.7, 1.0 and 2.0, respectively), and that no exchange of TBA ions is carried out at the end of the reaction. The solid product obtained is recovered by filtration and washed repeatedly in acetone and the product is dried under vacuum.

300 mg of each HA-PLA product prepared by using 5.2, 7.2 and 14.0 g of PLA-NHS are dissolved in 24 ml of anhydrous DMSO under argon, obtaining three solutions. Apart are prepared three solutions of different concentration of PEG-NH$_2$, obtained by dissolving in 6 ml of anhydrous DMSO, respectively, 0.42, 0.43 and 0.84 g of PEG-NH$_2$ of average molecular weight 5000 Da. to each of the three solutions is added dropwise a solution. The three PEG-NH$_2$ solutions are added dropwise to the HA-PLA solutions, with the proviso that PEG-NH$_2$ solutions of higher concentration are added to solutions of HA-PLA products obtained with higher amount of PLA-NHS. The reaction is carried out in the presence of DCC and NHS activators added in quantities equimolar to the PEG-NH$_2$ used. After 24 hours at ambient temperature, the reaction mixture is brought to 5° C. for 10 min to facilitate precipitation of the dicyclohexylurea (DCU) formed, which is then removed from the reaction mixture by filtration. Subsequently, the filtered reaction mixture is eluted in Dowex 50W×8-200 sodium resin to remove the TBA and the eluate is dialyzed against water using a Spectra/por Tubing dialysis membrane with cut-off of 3.5 kDa, to completely remove DMSO. The product recovered after freeze-drying is dissolved in water and eluted in Dowex 50W×8-200 acid resin; the eluate is finally purified by dialysis against concentrated NaCl solutions (5% w/v) for three days and against bidistilled water for the last two days, using a Spectra/por Tubing 12000/14000 Da dialysis membrane. The solution is finally dried by freeze-drying, and the obtained PEG-HA-PLA derivative shows the following data at $^1$H-NMR analysis [THF-d$_8$/D$_2$O 1/1]: δ 1.4 and 1.6 [2d, 3H, —O—CO—CH(CH$_3$)—O— of PLA], δ 2.1 (s, 3H, —NH—CO—CH$_3$ of HA), δ 4.0 (m, 4H, —CH$_2$—CH$_2$— of PEG), δ 5.40 [m, 1H, —O—COCH(CH$_3$)— of PLA].

The three different derivatives obtained are named in the following PEG-HA-PLA$_{(D)}$, PEG-HA-PLA$_{(E)}$ and PEG-HA-PLA$_{(F)}$. The derivatization degree (DD, %) in PEG of the PEG-HA-PLA derivatives is obtained comparing the integrals of the two peaks relative to the protons attributable to the —CH$_2$—CH$_2$— portion of the PEG-NH$_2$ (δ 4.0), with the integral relative to the protons (δ 2.1) attributable to the —NHCOCH$_3$ group pertaining to the HA N-acetylglucosamine residues, and then applying the formula:

DD=(No. moles PEG/No. moles glucosamine units)×100.

The results of derivatization degree for the three different reaction mixtures are as given in Table 2:

TABLE 2

| Sample | DD (%) in PLA | DD (%) in PEG |
|---|---|---|
| PEG-HA-PLA$_{(D)}$ | 5 | 9 |
| PEG-HA-PLA$_{(E)}$ | 7.2 | 9 |
| PEG-HA-PLA$_{(F)}$ | 13.9 | 17.9 |

EXAMPLE 5

This example describes the preparation of hydrogels from a HA derivative of the invention, the incorporation of an antibiotic into said hydrogel and the use of the latter to coat a series of specimens of a material used for making prostheses, and shows the results of antibiotic release from said coatings.

A hydrogel is produced with the derivative HA-PLA$_{(B)}$ prepared as described in example 3, by dispersing 40 mg of the starting HA-PLA$_{(B)}$ derivative in 0.9 ml of sterile (bidistilled) water until a transparent viscous gel is formed. Separately, a solution is prepared by dissolving 10 mg of the known antibiotic vancomycin (in the form of a powder for intravenous infusion solutions) in 0.1 ml of sterile water, and agitating the system until the solution becomes transparent; the resulting vancomycin solution has a concentration of 10% w/v. 0.1 ml of the vancomycin solution are then added to the HA-PLA$_{(B)}$ hydrogel, and the mixture agitated for a few minutes to facilitate drug incorporation into the gel. The antibacterial hydrogel thus obtained has a concentration of 4% w/v of the HA-PLA$_{(B)}$ derivative, and of 1% w/v in vancomycin. This antibacterial hydrogel is then manually spread with a spatula to uniformly cover the entire surface of three equal titanium specimens, each having the form of a circular disk with a surface of approximately 1 cm$^2$; the three specimens are weighted after having been coated with the antibacterial hydrogel, so that the initial amount of antibiotic loaded in any specimen is known. The thus prepared specimens are then introduced in three separated beakers, each containing 6 ml of DPBS pH 7.4; the temperature is kept at 37° C. throughout the test. At preset times (in the range 2-96 hours), 1 ml of the solution supernatant each disk is sampled, and the quantity of released drug contained therein is determined by HPLC analysis (after each sampling, the volume of solution supernatant the specimen is restored by addition of a volume of fresh DPBS solution equivalent to the sampled volume). The results of the release test are given in Table 3, both as average concentration (with indication of standard deviation) of antibiotic in solution (in mg/l) at the given sampling time, and as cumulative amount (%) of antibiotic released with time over the starting amount.

TABLE 3

| Sampling time | Vancomycin release (loading of vancomycin = 1% w/v) | |
|---|---|---|
| (hours) | mg/l | % |
| 2 | 316 ± 16 | 63 |
| 4 | 448 ± 23 | 89 |
| 24 | 470 ± 20 | 93 |
| 48 | 501 ± 16 | 100 |

The results in Table 3 show that the antibacterial hydrogel produced as described takes about 48 hours to completely release the antibiotic; the following table (Table 4) shows the amount of antibiotic released by this antibacterial hydrogel in time intervals elapsed between two next samplings:

TABLE 4

| Interval between sampling (hours) | Vancomycin release (mg/l) |
|---|---|
| 0-2 | 316 |
| 2-4 | 132 |
| 4-24 | 22 |
| 24-48 | 31 |

EXAMPLE 6

The procedure of Example 5 is repeated, using in this case a vancomycin solution prepared by dissolving 20 mg of the antibiotic in 0.1 ml of sterile water, thus doubling the loading of vancomycin in the antibacterial hydrogel. The results of antibiotic release with time are presented in Table 5:

TABLE 5

| Sampling time | Vancomycin release (loading of vancomycin = 2% w/v) | |
|---|---|---|
| (hours) | mg/l | % |
| 2 | 478 ± 16.6 | 80 |
| 4 | 520 ± 9.0 | 87 |
| 24 | 593 ± 16.0 | 100 |

The amount of antibiotic released in the intervals between next samplings in this case are given in table 6.

TABLE 6

| Interval between sampling (hours) | Vancomycin release (mg/l) |
|---|---|
| 0-2 | 478 |
| 2-4 | 42 |
| 4-24 | 73 |

EXAMPLE 7

Example 5 is repeated, using in this case a solution of NaOH in place of bidistilled water for the preparation of the hydrogel containing HA-PLA$_{(B)}$; this is done in order to change each carboxylic group of HA into the corresponding Na$^+$ salt, as this latter better binds the antibiotic (present in hydrochloride form), thus prolonging the period of release of the same. The results of antibiotic release with time for this antibacterial hydrogel are presented in Table 7:

TABLE 7

| Sampling time | Vancomycin release (loading of vancomycin = 1% w/v) | |
|---|---|---|
| (hours) | mg/l | % |
| 2 | 165 ± 16 | 54.5 |
| 4 | 203 ± 3 | 67.5 |
| 24 | 275 ± 7 | 91 |
| 48 | 288 ± 5 | 95 |
| 72 | 301 ± 2 | 100 |

The amount of antibiotic released in the intervals between next samplings for these three specimens are given in table 8:

TABLE 8

| Interval between sampling (hours) | Vancomycin release (mg/l) |
|---|---|
| 0-2 | 165 |
| 2-4 | 38 |
| 4-24 | 72 |
| 24-48 | 13 |
| 48-72 | 13 |

EXAMPLE 8

Example 7 is repeated, loading in this case the hydrogel with 2% w/v of vancomycin. The results of antibiotic release for these three specimens are given in Table 9:

TABLE 9

| Sampling time | Vancomycin release (loading of vancomycin = 2% w/v) | |
|---|---|---|
| (hours) | mg/l | % |
| 2 | 380 ± 45 | 50 |
| 4 | 601 ± 9 | 73 |
| 24 | 643 ± 10 | 84.6 |
| 48 | 756 ± 16 | 100 |

The amounts of antibiotic released in the intervals between next samplings in this case are given in table 10:

TABLE 10

| Interval between sampling (hours) | Vancomycin release (mg/l) |
|---|---|
| 0-2 | 380 |
| 2-4 | 221 |
| 4-24 | 42 |
| 24-48 | 113 |

EXAMPLE 9

Example 8 is repeated, with an antibacterial hydrogel having a HA-PLA$_{(B)}$ concentration equal to 10% w/v instead of 4% w/v. The results of antibiotic release with time for these three specimens are reported in Table 11:

TABLE 11

| Sampling time (hours) | Vancomycin release (loading of vancomycin = 2% w/v) | |
|---|---|---|
| | mg/l | % |
| 2 | 305 ± 16 | 47 |
| 4 | 433 ± 10 | 67 |
| 24 | 562 ± 25 | 87 |
| 48 | 640 ± 9 | 100 |

EXAMPLE 10

Example 5 is repeated, using in this case the derivative HA-PLA$_{(C)}$ prepared as described in example 3. Two antibacterial hydrogels are prepared and tested, having concentration equal to 4% and 6% w/v of the HA derivative respectively. The results of antibiotic release are reported in Table 12:

TABLE 12

| Sampling time (hours) | Vancomycin release (loading of vancomycin = 1% w/v) | | | |
|---|---|---|---|---|
| | 4% w/v HA-PLA$_{(C)}$ | | 6% w/v HA-PLA$_{(C)}$ | |
| | mg/l | % | mg/l | % |
| 2 | 288 ± 5 | 72 | 203 ± 1 | 66 |
| 4 | 310 ± 0.8 | 78 | 255 ± 17 | 83 |
| 24 | 360 ± 18 | 91 | 296 ± 0.5 | 97 |
| 48 | 395 ± 4 | 100 | 298 ± 3.5 | 98 |
| 72 | / | / | 305 ± 3.5 | 100 |

The amount of antibiotic released in the intervals between next samplings for three specimens prepared with 6% w/v HA-PLA$_{(C)}$ are given in table 13:

TABLE 13

| Interval between sampling (hours) | Vancomycin release (mg/l) |
|---|---|
| 0-2 | 203 |
| 2-4 | 52 |
| 4-24 | 41 |
| 24-48 | 2 |
| 48-72 | 7 |

EXAMPLE 11

Example 10 is repeated with an antibacterial hydrogel containing HA-PLA$_{(C)}$ at concentration 6% w/v and vancomycin at concentration 2%. The results of antibiotic release are reported in Table 14:

TABLE 14

| Sampling time (hours) | Vancomycin release (loading of vancomycin = 2% w/v) | |
|---|---|---|
| | mg/l | % |
| 2 | 299 ± 7 | 59 |
| 4 | 376 ± 9 | 74.3 |
| 24 | 482 ± 10 | 95.3 |
| 48 | 518 ± 08 | 100 |

The amounts of antibiotic released in the intervals between next samplings in this case are given in table 15:

TABLE 15

| Interval between sampling (hours) | Vancomycin release (mg/l) |
|---|---|
| 0-2 | 299 |
| 2-4 | 77 |
| 4-24 | 106 |
| 24-48 | 36 |

EXAMPLE 12

Example 9 is repeated, using in this case a HA-PLA$_{(C)}$ in place of HA-PLA$_{(B)}$ for the preparation of the hydrogel. The results of antibiotic release with time for this antibacterial hydrogel are reported in Table 16:

TABLE 16

| Sampling time (hours) | Vancomycin release (loading of vancomycin = 2% w/v) | |
|---|---|---|
| | mg/l | % |
| 2 | 350 ± 2 | 56.2 |
| 4 | 443 ± 12 | 73 |
| 24 | 530 ± 16 | 87 |
| 48 | 618 ± 7 | 99 |
| 72 | 632 ± 5 | 100 |

The amounts of antibiotic released in the intervals between next samplings in this case are given in table 17:

TABLE 17

| Interval between sampling (hours) | Vancomycin release (mg/l) |
|---|---|
| 0-2 | 350 |
| 2-4 | 93 |
| 4-24 | 87 |
| 24-48 | 88 |
| 48-72 | 14 |

EXAMPLE 13

This example is about the release of an antibiotic from an antibacterial hydrogel prepared with a HA derivative obtained by grafting onto the HA chain both a polyester and PEG.

Example 5 is repeated, using the derivative PEG-HA-PLA$_{(D)}$ prepared as described in Example 4; only the antibacterial hydrogel at concentration 4% w/v of HA derivative is tested. The results of antibiotic release with time for three specimens prepared with this antibacterial hydrogel are reported in Table 18:

TABLE 18

| Sampling time (hours) | Vancomycin release (loading of vancomycin = 1% w/v) | |
|---|---|---|
| | mg/l | % |
| 2 | 212 ± 12 | 55 |
| 4 | 303 ± 3 | 80 |
| 24 | 340 ± 7 | 89 |
| 48 | 353 ± 4 | 93 |
| 72 | 379 ± 2 | 100 |

The amounts of antibiotic released in the intervals between next samplings in this case are given in table 19:

TABLE 19

| Interval between sampling (hours) | Vancomycin release (mg/l) |
|---|---|
| 0-2 | 212 |
| 2-4 | 91 |
| 4-24 | 37 |
| 24-48 | 13 |
| 48-72 | 26 |

EXAMPLE 14

Example 13 is repeated using an antibacterial hydrogel with a vancomycin concentration of 2% w/v. The results of antibiotic release with time for this antibacterial hydrogel are reported in Table 20:

TABLE 20

| Sampling time | Vancomycin release (loading of vancomycin = 2% w/v) | |
|---|---|---|
| (hours) | mg/l | % |
| 2 | 416 ± 5 | 54.1 |
| 4 | 614 ± 26 | 79 |
| 24 | 698 ± 15 | 89.9 |
| 48 | 720 ± 8 | 92 |
| 72 | 778 ± 10 | 100 |

The amounts of antibiotic released in the intervals between next samplings for these three specimens are given in table 21:

TABLE 21

| Interval between sampling (hours) | Vancomycin release (mg/l) |
|---|---|
| 0-2 | 416 |
| 2-4 | 198 |
| 4-24 | 84 |
| 24-48 | 22 |
| 48-72 | 58 |

EXAMPLE 15

This example is about the release of an antibiotic from an antibacterial hydrogel prepared with a HA derivative obtained by grafting a polyester onto HA of higher molecular weight than as used in the previous examples.

The procedure of Example 1 is repeated, using however as starting material the HA sodium salt of MW 1500 kDa, not previously subjected to degradation in HCl. The HA-TBA salt thus produced is reacted with PLA-NHS as described in Example 3, with a nominal mole ratio PLA-NHS to N-acetyl-D-glucosamine units equal to 1.5; the resulting derivatization degree is of 7%. This derivative, named HA-PLA$_{(G)}$, is then diluted with bidistilled water and added with a vancomycin solution, to obtain an antibacterial hydrogel with HA-PLA$_{(G)}$ concentration of 10% w/v and vancomycin concentration of 2% w/v. This antibacterial hydrogel is used to coat a titanium disk that is then subjected to a drug release test as described in Example 5. The results of the test are given in Table 22:

TABLE 22

| Sampling time | Vancomycin release (loading of vancomycin = 2% w/v) | |
|---|---|---|
| (hours) | mg/l | % |
| 2 | 496 ± 5 | 80 |
| 4 | 508 ± 2 | 82 |
| 24 | 578 ± 1 | 93 |
| 48 | 611 ± 2 | 98 |
| 72 | 618 ± 12 | 100 |

The amounts of antibiotic released in the intervals between next samplings for these three specimens are given in table 23:

TABLE 23

| Interval between sampling (hours) | Vancomycin release (mg/l) |
|---|---|
| 0-2 | 496 |
| 2-4 | 12 |
| 4-24 | 70 |
| 24-48 | 33 |
| 48-72 | 7 |

EXAMPLE 16

This example is about the release of another antibiotic from an antibacterial hydrogel of the invention.

A procedure similar to that described in Example 6 is repeated, using in this case tobramycin in place of vancomycin for the preparation of the antibacterial hydrogel; only the antibacterial hydrogel at concentration 4% w/v of HA derivative is tested.

HA-PLA$_{(B)}$ as prepared in Example 3 is dissolved in bidistilled water to obtain a solution of concentration 6.67% w/v. 0.6 ml of this solution are mixed with 0.4 ml of a commercial solution of tobramycin of concentration 50 mg/ml, obtaining an antibacterial hydrogel with concentration 4% w/v of HA-PLA$_{(B)}$ and 2% w/v of tobramycin. A titanium disk as in the previous examples is coated with this antibacterial hydrogel. The results of antibiotic release with time for these three specimens are reported in Table 24:

TABLE 24

| Sampling time | Tobramycin release (loading of tobramycin = 2% w/v) | |
|---|---|---|
| (hours) | mg/l | % |
| 2 | 332 ± 5 | 54 |
| 4 | 567 ± 10 | 92.6 |
| 24 | 606 ± 2 | 99 |
| 48 | 609 ± 2 | 99.5 |
| 72 | 612 ± 1 | 100 |

The amounts of antibiotic released in the intervals between next samplings for the three specimens prepared with tobramycin are given in table 25:

TABLE 25

| Interval between sampling (hours) | Tobramycin release (mg/l) |
|---|---|
| 0-2 | 332 |
| 2-4 | 235 |

TABLE 25-continued

| Interval between sampling (hours) | Tobramycin release (mg/l) |
|---|---|
| 4-24 | 39 |
| 24-48 | 3 |
| 48-72 | 3 |

EXAMPLE 17

Example 16 is repeated, using in this case an antibacterial hydrogel with a HA derivative concentration of 6% w/v loaded with tobramycin at 2% w/v. The antibacterial hydrogel is prepared by mixing 0.6 ml of a solution 10% w/v of HA-PLA$_{(B)}$ with 0.4 ml of the same commercial solution of tobramycin employed in the previous example. The results of antibiotic release with time for the three specimens thus obtained are given in Table 26:

TABLE 26

| Sampling time | Tobramycin release (loading of tobramycin = 2% w/v) | |
|---|---|---|
| (hours) | mg/l | % |
| 2 | 281 ± 21 | 58 |
| 4 | 397 ± 3 | 82 |
| 24 | 466 ± 1 | 96 |
| 48 | 471 ± 6 | 97 |
| 72 | 484 ± 6 | 100 |

The amounts of antibiotic released in the intervals between next samplings for these three specimens are given in table 27:

TABLE 27

| Interval between sampling (hours) | Tobramycin release (mg/l) |
|---|---|
| 0-2 | 281 |
| 2-4 | 116 |
| 4-24 | 69 |
| 24-48 | 5 |
| 48-72 | 13 |

EXAMPLE 18

Example 12 is repeated, using tobramycin in place of vancomycin for the preparation of the antibacterial hydrogel. This is obtained by mixing 0.6 ml of a solution of HA-PLA$_{(C)}$ of concentration 6.67% w/v with 0.4 ml of the commercial solution of tobramycin of Example 16. The results of antibiotic release with time for the three specimens prepared with this antibacterial hydrogel are given in Table 28:

TABLE 28

| Sampling time | Tobramycin release (loading of tobramycin = 2% w/v) | |
|---|---|---|
| (hours) | mg/l | % |
| 2 | 252 ± 34 | 54 |
| 4 | 360 ± 41 | 78 |
| 24 | 404 ± 16 | 87 |
| 48 | 444 ± 10 | 96 |
| 72 | 463 ± 13 | 100 |

The amounts of antibiotic released in the intervals between next samplings for these three specimens are given in table 29:

TABLE 29

| Interval between sampling (hours) | Tobramycin release (mg/l) |
|---|---|
| 0-2 | 252 |
| 2-4 | 108 |
| 4-24 | 44 |
| 24-48 | 40 |
| 48-72 | 19 |

EXAMPLE 19

This example is about the combined release of two antibiotics from an antibacterial hydrogel prepared with a HA derivative obtained by grafting PLA onto HA.

A hydrogel is prepared by treating derivative HA-PLA$_{(B)}$ (prepared as described in example 3) with a solution of NaOH as in example 7. This hydrogel is then loaded with both vancomycin and tobramycin following the procedures described in examples 5 and 16, respectively, obtaining an antibacterial hydrogel of concentration 8% w/v in HA derivative, 1% w/v in vancomycin and 1% w/v in tobramycin. This antibacterial hydrogel is used to coat three equal titanium specimens, subsequently tested for antibiotics release, following the procedure described in example 5. The results of antibiotics release with time are given in Table 30:

TABLE 30

| Sampling time | 8% w/v HA-PLA$_{(B)}$ vancomycin = 1% w/v, tobramycin = 1% w/v | | | |
|---|---|---|---|---|
| (hours) | mg/l | % | mg/l | % |
| 2 | 90 ± 22 | 26.8 | 81 ± 17 | 35.8 |
| 4 | 169 ± 6 | 50.4 | 89 ± 25 | 39.4 |
| 24 | 252 ± 17 | 75.2 | 198 ± 30 | 87.6 |
| 48 | 300 ± 20 | 89.5 | 219 ± 10 | 96.9 |
| 72 | 326 ± 10 | 97.3 | 226 ± 12 | 100 |
| 96 | 335 ± 1 | 100 | / | / |

EXAMPLE 20

Example 19 is repeated, using in this case an antibacterial hydrogel with a HA derivative concentration of 10% w/v loaded with vancomycin and tobramycin both at 2% w/v. The results of antibiotics release with time are given in Table 31:

TABLE 31

| Sampling time | 10% w/v HA-PLA$_{(B)}$ vancomycin = 2% w/v, tobramycin = 2% w/v | | | |
|---|---|---|---|---|
| (hours) | mg/l | % | mg/l | % |
| 2 | 413 ± 7 | 56.6 | 385 ± 55 | 76.7 |
| 4 | 611 ± 34 | 83.8 | 389 ± 27 | 77.5 |
| 24 | 689 ± 34 | 94.5 | 475 ± 22 | 94.6 |
| 48 | 715 ± 22 | 98.1 | 502 ± 64 | 100 |
| 72 | 729 ± 27 | 100 | / | / |

The amounts of the two antibiotics released in the intervals between next samplings in this case are given in table 32:

TABLE 32

| Interval between sampling (hours) | Vancomycin release (mg/l) | Tobramycin release (mg/l) |
|---|---|---|
| 0-2 | 413 | 385 |
| 2-4 | 198 | 4 |
| 4-24 | 78 | 86 |
| 24-48 | 26 | 27 |
| 48-72 | 14 | / |

EXAMPLE 21

Example 19 is repeated, using in this case a hydrogel prepared with derivative HA-PLA$_{(C)}$ (prepared as described in example 3) treated with bidistelled water instead of a NaOH solution; the final antibacterial hydrogel has a HA derivative concentration of 6% w/v and vancomycin and tobramycin concentrations both equal to 1% w/v. The results of antibiotics release with time are given in Table 33:

TABLE 33

| Sampling time | 6% w/v HA-PLA$_{(C)}$ vancomycin = 1% w/v, tobramycin = 1% w/v | | | |
|---|---|---|---|---|
| (hours) | mg/l | % | mg/l | % |
| 2 | 192 ± 7 | 48.5 | 151 ± 30 | 62.1 |
| 4 | 308 ± 52 | 77.7 | 176 ± 15 | 72.4 |
| 24 | 380 ± 33 | 95.9 | 243 ± 26 | 100 |
| 48 | 393 ± 21 | 99.2 | / | / |
| 72 | 396 ± 12 | 100 | / | / |

The amounts of the two antibiotics released in the intervals between next samplings in this case are given in table 34:

TABLE 34

| Interval between sampling (hours) | Vancomycin release (mg/l) | Tobramycin release (mg/l) |
|---|---|---|
| 0-2 | 192 | 151 |
| 2-4 | 116 | 25 |
| 4-24 | 72 | 67 |
| 24-48 | 13 | / |
| 48-72 | 3 | / |

EXAMPLE 22

Example 21 is repeated, with the difference that in this case the concentration of the two antibiotics is doubled. The results of antibiotics release with time are given in Table 35:

TABLE 35

| Sampling time | 6% w/v HA-PLA$_{(C)}$ vancomycin = 2% w/v, tobramycin = 2% w/v | | | |
|---|---|---|---|---|
| (hours) | mg/l | % | mg/l | % |
| 2 | 258 ± 33 | 46.5 | 117 ± 59 | 29.7 |
| 4 | 426 ± 36 | 76.7 | 238 ± 31 | 60.5 |
| 24 | 500 ± 21 | 90.0 | 301 ± 7 | 76.6 |
| 48 | 555 ± 30 | 100 | 393 ± 12 | 100 |

The amounts of the two antibiotics released in the intervals between next samplings in this case are given in table 36:

TABLE 36

| Interval between sampling (hours) | Vancomycin release (mg/l) | Tobramycin release (mg/l) |
|---|---|---|
| 0-2 | 258 | 117 |
| 2-4 | 168 | 121 |
| 4-24 | 74 | 63 |
| 24-48 | 55 | 92 |

EXAMPLE 23

Example 22 is repeated, with the differences that derivative PEG-HA-PLA$_{(D)}$ (prepared as described in example 4) is used, and that its concentration in the antibacterial hydrogel is 4% w/v. The results of antibiotics release with time are given in Table 37:

TABLE 37

| Sampling time | 4% w/v PEG-HA-PLA$_{(D)}$ vancomycin = 2% w/v, tobramycin = 2% w/v | | | |
|---|---|---|---|---|
| (hours) | mg/l | % | mg/l | % |
| 2 | 581 ± 95 | 80.0 | 359 ± 42 | 62.0 |
| 4 | 713 ± 42 | 98.2 | 396 ± 42 | 68.4 |
| 24 | 726 ± 20 | 100 | 579 ± 154 | 100 |

The amounts of the two antibiotics released in the intervals between next samplings in this case are given in table 38:

TABLE 38

| Interval between sampling (hours) | Vancomycin release (mg/l) | Tobramycin release (mg/l) |
|---|---|---|
| 0-2 | 581 | 359 |
| 2-4 | 132 | 37 |
| 4-24 | 13 | 183 |

Discussion of Results

The chemical derivatization of hyaluronic acid (HA) with polyesters (in particular polylactic acid, PLA) leads to the formation of copolymers which when contacted with an aqueous medium (e.g., bidistilled water, a physiological solution at pH 7.4 or a NaOH solution) can be used to produce antibacterial hydrogels with promising applications in the orthopedic field. These antibacterial hydrogels are in fact easily prepared by simply adding the HA-polyester copolymers to aqueous or physiological solutions, are transparent, easily spreadable over a surface (for example a titanium prosthesis) and have the capacity of incorporating and releasing in a protracted manner drugs incorporated into them.

In particular, examples 5 through 15 show that antibacterial hydrogels containing HA-polyester (in particular HA-PLA) polymers with different degree of derivatization with the polyester, possible co-derivatization with PLA and PEG, different concentration of the HA derivative, and different concentrations of vancomycin, release suitable drug quantities soon after the implant of the prosthesis. This result is very important as a good initial burst effect could ensure efficient drug action in the hours immediately following implanting of the prosthesis, the period in which the establishment of a bacterial infection is most probable. Moreover, during the entire drug release period, the antibiotic concentration released by the antibacterial hydrogel is always greater than the minimum inhibiting concentration (MIC), thus ensuring effectiveness of the drug released in proximity to the prosthesis; these MIC values are known from the literature and are, respectively, in the range 1.56-3.12 mg/l for vancomycin (see the paper "In vivo study of hot compressing molded 50:50 poly (DL-lactide-co-glycolide) antibiotic beads in rabbits", Steve W. N. et al, Journal of Orthopaedic Research (2002) 20: 654-661) and of about 1 mg/l for tobramycin (see the paper "Evaluation of once daily tobramycin dosing in critically ill patients through Bayesian simulation", Peris-Marti J. F. et al, Journal of Clinical Pharmacy and Therapeutics (2004) 29: 65-70). Examples 16-18 and 19-23 show similar results, respectively, for tobramycin alone and for vancomycin and tobramycin used in combination.

More in detail, from the tests it can be noted that particularly good results can be obtained with the use of a NaOH solution in place of pure water for producing the hydrogel (compare, for instance, the results in examples 5 and 7 for vancomycin, and those in examples 19 and 21 for the combined use of vancomycin and tobramycin). Similarly, very good results are obtained with the use of derivatives obtained by grafting onto HA chains both a polyester (PLA) and polyethylene glycol.

Another general trend that is noted in the examples is that increasing the amount of antibiotic initially loaded in the antibacterial hydrogel leads to an increased rate of release of the same; however, the levels of antibiotic in solution are always higher than the MIC value for the antibiotics.

The invention claimed is:

1. An antibacterial hydrogel comprising water, a hyaluronic acid derivative and an antibacterial agent, wherein:
   the hyaluronic acid derivative comprises hyaluronic acid, or a salt thereof, of molecular weight comprised between 50,000 and 3,500,000 Da, and chains of a biodegradable and biocompatible polyester of molecular weight comprised between 3,000 and 900,000 Da grafted onto the N-acetyl-D-glucosamine moieties only of said hyaluronic acid or salt thereof, in an amount such that the derivative comprises between 1 and 15 of said polyester chains per 100 repeating unit D-glucuronic acid/N-acetyl-D-glucosamine of hyaluronic acid;
   the concentration of said hyaluronic acid derivative or salt thereof is comprised between 1 and 30% w/v; and
   the antibacterial agent is selected from the group consisting of antibiotics, antifungals metal ions and their combinations and has a concentration comprised between 0.001% and 80% w/v.

2. The antibacterial hydrogel according to claim 1, wherein the concentration of said hyaluronic acid derivative or salt thereof is comprised between 2 and 10%.

3. The antibacterial hydrogel according to claim 1, wherein said hyaluronic acid or salt thereof has molecular weight comprised between 100,000 Da and 1,500,000 Da.

4. The antibacterial hydrogel according to claim 3, wherein said molecular weight is comprised between 200,000 Da and 300,000 Da.

5. The antibacterial hydrogel according to claim 1, wherein said polyester is selected from the group consisting of polylactic acid of molecular weight in the range between 3,000 and 150,000 Da, poly-glycolic acid of molecular weight in the range between 3,000 and 900,000 Da, poly-caprolactone of molecular weight in the range between 3,000 and 900,000 Da, mixtures and copolymers thereof.

6. The antibacterial hydrogel according to claim 1, wherein onto the D-glucuronic acid moieties only of said hyaluronic acid or salt thereof are further grafted chains of polyethylene glycol.

7. The antibacterial hydrogel according to claim 6, wherein said polyethylene glycol has molecular weight in the range between 400 Da and 20,000 Da.

8. The antibacterial hydrogel according to claim 6, wherein the ratio of D-glucuronic acid units to which is grafted a polyethylene glycol chain to the total number of such units present in the hyaluronic acid (HA) chain is comprised between 5 and 20%.

9. The antibacterial hydrogel according to claim 1, wherein said water is added to said hyaluronic acid derivative in the form of bidistilled water, or of a NaOH solution of concentration between 0.075 and 0.75 M/l, or a physiological solution.

10. The antibacterial hydrogel according to claim 1, wherein said antibacterial agent is:
    an antibiotic which is a glicopeptide, an aminoglicosyde, a cephalosporin, a macrolids oxazolidinone, a quinolone, a polymixin, a sulfonamide, a tetracycline or a penicillin selected from the group consisting of daptomicin, tigecycline, telavancin, chloramphenicol, fusidic acid, bacitracin, rifampin, ethambutol, streptomycin, isoniazid; or
    an antifungal selected from the group consisting of polyene antifungals, imidazole and triazole antifungals, allylamines, echinocandines and griseofulvine; or
    a metal selected from the group consisting of silver and nanosilver formulations, zinc, copper, cobalt and nickel.

11. A method for using the antibacterial hydrogel of claim 1, characterized in that, when the antibacterial agent is an antibiotic:
    said antibacterial hydrogel is produced by mixing in the desired ratio a hydrogel comprising the hyaluronic acid (HA) derivative in water with the chosen antibacterial agent, and
    in a short term after said mixing operation, the antibacterial hydrogel is injected in the area of a bone fracture or cavity or applied to the surface of a prosthesis to be implanted.

12. The method of claim 11, characterized in that when the antibacterial hydrogel is applied onto a prosthesis, this operation is carried out by a method chosen among immersion of the prosthesis into the hydrogel, spraying, spreading and brushing.

13. A kit for use in the method of claim 11 comprising two compositions, the first one being a hydrogel formed by the HA derivative and water having a concentration of HA derivative comprised between 1 and 35% w/v, the second one being or comprising the antibacterial agent.

14. The kit of claim 13, wherein said concentration of HA derivative is comprised between 2 and 10% w/v.

15. The kit of claim 13, wherein said second composition comprises the antibacterial agent, and is a solution or suspension of the latter.

16. A prosthesis for implant in the human or animal body coated with an antibacterial hydrogel according to the method of claim 11.

17. A kit for use in the method of claim 12 comprising two compositions, the first one being a hydrogel formed by the HA derivative and water having a concentration of HA derivative comprised between 1 and 35% w/v, the second one being or comprising the antibacterial agent.

18. The kit of claim 17, wherein said concentration of HA derivative is comprised between 2 and 10% w/v.

19. The kit of claim 17, wherein said second composition comprises the antibacterial agent, and is a solution or suspension of the latter.

20. A prosthesis for implant in the human or animal body coated with an antibacterial hydrogel according to the method of claim 12.

\* \* \* \* \*